United States Patent
Ooi et al.

[11] Patent Number: 6,066,744
[45] Date of Patent: May 23, 2000

[54] PROCESS FOR PRODUCING 5-METHYLINDOLINES

[75] Inventors: Hideo Ooi; Toshihisa Watanabe; Chikara Hijikata, all of Ihara-gun, Japan

[73] Assignee: Ihara Chemical Industry Co., Ltd., Tokyo, Japan

[21] Appl. No.: 09/402,456

[22] PCT Filed: Apr. 3, 1998

[86] PCT No.: PCT/JP98/01557

§ 371 Date: Oct. 7, 1999

§ 102(e) Date: Oct. 7, 1999

[87] PCT Pub. No.: WO98/45261

PCT Pub. Date: Oct. 15, 1998

[30] Foreign Application Priority Data

Apr. 7, 1997 [JP] Japan .................................. 9-103838

[51] Int. Cl.[7] .................................................. C07D 209/08
[52] U.S. Cl. ............................................................ 548/490
[58] Field of Search ............................................... 548/490

[56] References Cited

U.S. PATENT DOCUMENTS 4,159,271  6/1979  Sano et al. ....................... 260/326.21

Primary Examiner—Laura L. Stockton
Attorney, Agent, or Firm—Oblon, Spivak, McClelland, Maier & Neustadt, P.C.

[57] ABSTRACT

Presentation of a method for producing a 5-methylindoline represented by the formula:

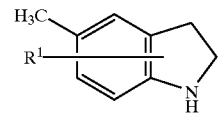

Ka-2

(wherein R is a hydrogen atom or a lower alkyl group), which comprises catalytically hydrogenating a 1-(substituted)benzyl-5-formylindoline represented by the formula:

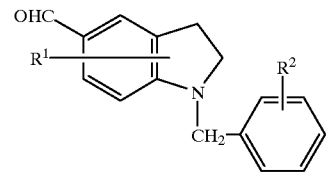

Ka-1

(wherein $R^1$ is a hydrogen atom or a lower alkyl group, and $R^2$ is a hydrogen atom, a lower alkyl group or a lower alkoxy group) in the presence of an inert solvent and a palladium catalyst.

1 Claim, No Drawings

PROCESS FOR PRODUCING 5-METHYLINDOLINES

This application is a 371 of PCT/JP/98/01557 filed Apr. 3, 1998.

TECHNICAL FIELD

The present invention relates to a method for producing a 5-methylindoline which is very useful as an intermediate for medical and agricultural chemicals.

BACKGROUND ART

Heretofore, various methods have been proposed as methods for producing 5-methylindolines, but none of such methods has reached a level for practical industrial application.

DISCLOSURE OF THE INVENTION

It is an object of the present invention to provide a novel method for industrially producing a 5-methylindoline simply from a starting material which is industrially readily available.

To accomplish the above object, the present inventors have conducted extensive researches and as a result, have found it possible to carry out a reduction reaction to convert the formyl group at the 5-position of the indoline structure to a methyl group and a benzyl-removing reaction to remove the benzyl moiety at the 1-position of the indoline structure at the same time, by catalytically hydrogenating, in the presence of an inert solvent and a palladium catalyst, a 1-(substituted)benzyl-5-formylindoline (ka-3) which can be industrially produced by formylating the 5-position and converting the 1-position of the corresponding indoline to a (substituted)benzyl group. The present invention has been accomplished on the basis of this discovery.

Namely, the present invention has accomplished the above object by presenting a method for producing a 5-methylindoline represented by the formula:

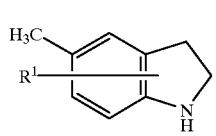

Ka-4

(wherein $R^1$ is a hydrogen atom or a lower alkyl group), which comprises catalytically hydrogenating a 1-(substituted)benzyl-5-formylindoline represented by the formula:

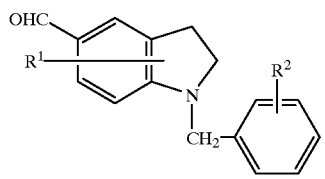

Ka-3

(wherein $R^1$ is a hydrogen atom or a lower alkyl group, and $R^2$ is a hydrogen atom, a lower alkyl group or a lower alkoxy group) in the presence of an inert solvent and a palladium catalyst.

BEST MODE FOR CARRYING OUT THE INVENTION

Now, the method of the present invention will be described in detail.

The method of the present invention is a novel method for producing a 5-methylindoline, which comprises catalytically hydrogenating a 1-(substituted)benzyl-5-formylindoline (ka-3) which is readily industrially available as a starting material, in the presence of an inert solvent and a palladium catalyst.

As the 1-(substituted)benzyl-5-formylindoline (ka-3) to be used as the starting material in the method of the present invention, any 1-(substituted)benzyl-5-formylindoline may be employed so long as $R^1$ in the formula (ka-3) is a hydrogen atom or a $C_{1-6}$ lower alkyl group, such as a methyl group, an ethyl group, a n-propyl group, an isopropyl group, a n-butyl group, an isobutyl group, a pentyl group or a hexyl group, and $R^2$ is a hydrogen atom; a $C_{1-6}$ lower alkyl group, such as a methyl group, an ethyl group, a n-propyl group, an isopropyl group, a n-butyl group, an isobutyl group, a pentyl group or a hexyl group; or a $C_{1-6}$ lower alkoxy group, such as a methoxy group, an ethoxy group, a n-propoxy group, an isopropoxy group, a n-butoxy group, an isobutoxy group, a pentyloxy group or a hexyloxy group. As such a 1-(substituted)benzyl-5-formylindoline having $R^1$ and $R^2$ specifically, 1-benzyl-5-formylindoline, 1-benzyl-2-methyl-5-formylindoline or 1-(4'-methoxybenzyl)-2-methyl-5-formylindoline, may, for example, be mentioned. However, the starting material in the method of the present invention is not limited to such exemplified compounds.

As the palladium catalyst to be used in the method of the present invention, any palladium catalyst may be employed so long as it is used commonly in catalytic hydrogenation. In such a case, palladium may be used alone, or a simple substance or a hydroxide or the like of palladium, may be supported on a solid carrier such as active carbon, alumina, calcium carbonate, silica, diatomaceous earth or barium sulfate. In such a case, the proportion of palladium supported on the carrier, is not limited and may be suitably determined taking the reaction conditions or economical aspects into consideration. Conveniently, a commercially available catalyst for catalytic hydrogenation having palladium supported in a various proportion on active carbon, may, for example, be employed. The proportion of the palladium supported on a commercial product is usually from 2 to 10%, but as mentioned above, the proportion of palladium supported on the palladium catalyst to be used in the present invention, is not particularly limited. The palladium catalysts may be used alone or in admixture of two or more of them. Specifically, as palladium catalysts, Pd/C (one having palladium supported on active carbon), $Pd/Al_2O_3$ (one having palladium supported on alumina), $Pd(OH)_2/C$ (one having palladium hydroxide supported on active carbon), and $Pd/CaCO_3$ (one having palladium supported on calcium carbonate), may, for example, be mentioned. Among them, especially from the industrial viewpoint, it is advantageous to use Pd/C. With respect to the amount of the palladium catalyst, for example, in the case of using 5% (representing the amount of palladium supported)-Pd/C, it is from 0.1 to 40 wt %, preferably from 5 to 30 wt %, as the palladium catalyst, based on the 1-(substituted)benzyl-5-formylindoline (ka-3).

As the inert solvent to be used in the method of the present invention, a solvent which is commonly used for catalytic hydrogenation may be employed. For example, an alcohol such as methanol, ethanol, n-propanol, isopropanol, n-butanol, ethylene glycol, propylene glycol, 2-methoxyethanol or 2-ethoxyethanol; an aromatic hydrocarbon such as toluene, benzene or xylene; an aliphatic esters such as methyl acetate, ethyl acetate or butyl acetate; a polar solvent such as an ether type solvent such as dioxane, an aprotic polar solvent such as N,N-dimethylformamide (DMF), N,N-diethylformamide, 1,3-dimethyl-2-imidazolidinone (DMI), 1-methyl-2-pyrrolidone, 1,3-dimethyl-3,4,5,6-tetrahydro-2(1H)-pyrimidinone, N,N-dimethylacetamide (DMAC), N,N-diethylacetamide or 1,1,3,3-tetramethylurea, an organic acid such as acetic acid, or water; may be mentioned. Preferred is a lower aliphatic alcohol such as methanol, ethanol, n-propanol or isopropanol. The inert solvents may be used alone or in admixture of two or more of them, and to an inert solvent other than acetic acid, from 1 to 20 volume % of acetic acid or the like may be added. The amount of the inert solvent varies depending upon the type of the 5-formylindoline (ka-3), but may be at least an amount sufficient for stirring. Usually, it is used in an amount of from 0.1 to 2 λ, preferably from 0.5 to 1 λ, per mol of the 5-formylindoline (ka-3).

Further, the hydrogen is not particularly limited, and one which is readily industrially available, can be used as it is. One commercially available as filled in a bomb, is readily available and economical. Further, the method for introducing the hydrogen and the method for the reaction are not particularly limited, and the reaction may be carried out in accordance with a common method for catalytic hydrogenation under atmospheric pressure or elevated pressure. When a pressure reactor is to be employed, any reactor which is usually called as such, may be employed, but it is usual to employ an autoclave. The hydrogen pressure for the reaction may be adjusted so that the hydrogen pressure at the initiation of the reaction in the reactor is from atmospheric pressure to 50 kg/cm², preferably from atmospheric pressure to 10 kg/cm².

The reaction temperature can optionally be selected within a temperature range of at most the boiling point of the solvent, preferably within a range of from 0 to 150° C., more preferably from 50 to 100° C. The reaction time can not generally be defined as it differs depending upon various conditions such as the method for introducing the hydrogen, the activity of the catalyst, the initial pressure of the hydrogen, etc., but usually terminates in a few hours to a few tens hours. Generally, the higher the initial pressure of hydrogen, the shorter the reaction time. Practically, the time at which absorption of hydrogen has seized, may be taken as the terminal point.

The 5-methylindoline (ka-4) formed by this reaction may be taken out by e.g. a method of distilling a residue obtained by concentrating the solvent from the reaction solution, depending upon the inert solvent to be used in the reaction.

The 1-(substituted)benzyl-5-formylindoline (ka-3) to be used as the starting material in the method of the present invention can readily be available also industrially by using an indoline as the starting material, modifying the 1-position of the indoline structure with benzyl in accordance with e.g. a method disclosed in J. Org. Chem. vol. 33, (4), p. 1348 (1968), followed by formylating the 5-position of the indoline structure in accordance with e.g. a method disclosed in JP-A-6-41068, as shown by the following scheme (ka-5).

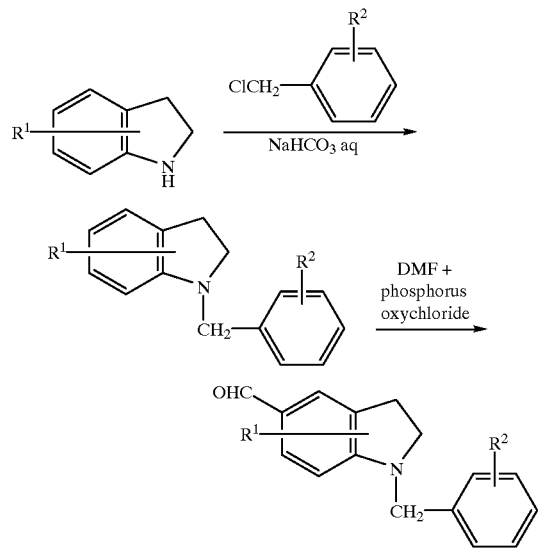

Ka-5

(wherein R is a hydrogen atom or a lower alkyl group, and R² is a hydrogen atom, a lower alkyl group or a lower alkoxy group.) The present invention provides a novel method for producing a 5-methylindoline, wherein a readily available 1-(substituted)benzyl-5-formylindoline which can be readily produced also industrially from a (substituted) indoline in only two steps, is used as the starting material, and such a starting material is catalytically hydrogenated in the presence of an inert solvent and a palladium catalyst. According to the method of the present invention, the reduction reaction of the formyl group at the 5-position of the indoline structure to a methyl group, and the reaction for removal of the benzyl moiety at the 1-position, can simultaneously be carried out in the same reactor, and besides, it has a merit that the desired product can be obtained in good yield even under such a condition as an atmospheric pressure reaction where the pressure in the reaction system is low, if necessary. The method of the present invention is excellent in the operation efficiency, simple and advantageous from the viewpoint of the energy and costs, as compared with the conventional methods, and thus is suitable for operation on an industrial scale. Thus, its value for industrial application is very high.

EXAMPLES

Now, the present invention will be described in further detail with reference to Examples and Reference Examples.

Example 1

Into a 200 mλ pressure resistant reactor (autoclave) equipped with a stirrer, 20 g (0.084 mol) of 1-benzyl-5-formylindoline and 100 mλ of ethanol were charged, and the interior of the reactor was flushed with nitrogen. 2 g of 10% Pd/C was introduced, and the reactor was closed, whereupon hydrogen was introduced from a hydrogen supply pipe and reacted at 80° C. for 6 hours while adjusting the initial pressure of hydrogen in the reactor to be 6 2 kg/cm. Upon confirming the ceasing of absorption of hydrogen, the reaction was terminated. Then, the reaction solution was cooled to room temperature, and the hydrogen was released, and the palladium catalyst (10% Pd/C) was collected by filtration, and ethanol was distilled off under reduced pressure to obtain a colorless liquid as the residue. The obtained liquid was subjected to vacuum distillation to obtain 9.5 g of 5-methylindoline having a boiling point of from 56 to 57° C./0.3 mmHg. The yield was 85% (based on 1-benzyl-5-formylindoline).

Example 2

The operation was carried out in the same manner as in Example 1 except that ethanol was changed to toluene. As a result, 9.5 g of 5-methylindoline was obtained. The yield was 85% (based on the 1-benzyl-5-formylindoline).

Example 3

Into a 200 mλ atmospheric pressure hydrogenation apparatus equipped with a thermometer and a stirrer, 2.0 g (0.0084 mol) of 1-benzyl-5-formylindoline, 0.4 g of 5% Pd/C and 100 mλ of ethanol were charged, and while introducing hydrogen under atmospheric pressure, a reaction was carried out at from 60 to 70° C. for 8 hours, and when the absorption of hydrogen ceased, the reaction was terminated. After termination of the reaction, the lo palladium catalyst (5% Pd/C) was collected by filtration, and ethanol was distilled off under reduced pressure to obtain a slightly red liquid. The obtained liquid was subjected to vacuum distillation to obtain 0.9 g of 5-methylindoline having a boiling point of 93° C./4 mmHg. The yield was 80.4% (based on the 1-benzyl-5-formylindoline).

Reference Example 1
[Preparation of 1-benzyl-5-formylindoline]
(Synthesis of 1-benzylindoline)

Into a 1,000 mλ reaction flask equipped with a thermometer, a stirrer, a condenser and a dropping funnel, 119.2 g (1.0 mol) of indoline, 105 g (1.25 mols) of sodium hydrogen carbonate and 200 g of water were charged, and the temperature was raised to a liquid temperature of 90° C. Then, while stirring at the same temperature, 132.9 g (1.05 mols) of benzyl chloride was dropwise added thereto over a period of about one hour from the dropping funnel, and then stirring was continued for eight hours at from 90 to 95° C. After completion of the reaction, 400 mλ of toluene was added, and the mixture was stirred from 60 to 80° C. for a while and then left to stand still for liquid separation. From the obtained organic layer, toluene was distilled off under reduced pressure to obtain 209 g of brown 1-benzylindoline (crude yield: 100%).

(Synthesis of 1-benzyl-5-formylindoline)

Into a 1,000 mλ reaction flask equipped with a thermometer, a stirrer, a condenser and a dropping funnel, 209 g (1.0 mol) of 1-benzylindoline and 365.5 g (5.0 mols) of N,N-dimethylformamide (DMF) were charged, and the temperature was raised to a liquid temperature of from 30 to 40° C. Then, while stirring at the same temperature, 161.0 g (1.05 mols) of phosphorus oxychloride was dropwise added thereto over a period of about two hours from the dropping funnel. After completion of the dropwise addition, stirring was continued for three hours at from 80 to 100° C. After completion of the reaction, the reaction solution was cooled to room temperature and put into 1 kg of ice water. At a temperature of from 30 to 40° C., a 24% sodium hydroxide aqueous solution was dropwise added thereto to bring the liquid alkaline, whereby the precipitated solid was collected by filtration, washed with water and dried to obtain 230.2 g (yield: 97%) of 1-benzyl-5 -formylindoline as a slightly yellow powder.

We claim:
1. A method for producing a 5-methylindoline represented by the formula:

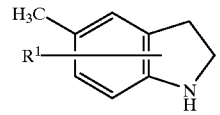

Ka-2

(wherein $R^1$ is a hydrogen atom or a lower alkyl group), which comprises catalytically hydrogenating a 1-(substituted)benzyl-5-formylindoline represented by the formula:

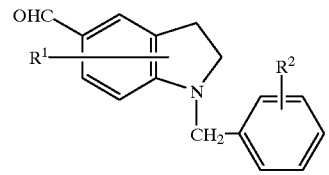

Ka-1

(wherein $R^1$ is a hydrogen atom or a lower alkyl group, and $R^2$ is a hydrogen atom, a lower alkyl group or a lower alkoxy group) in the presence of an inert solvent and a palladium catalyst.

* * * * *